United States Patent
Li et al.

(10) Patent No.: US 11,154,844 B2
(45) Date of Patent: Oct. 26, 2021

(54) COBALT CARBIDE-BASED CATALYST FOR DIRECT PREPARATION OF OLEFIN FROM SYNTHESIS GAS, PREPARATION METHOD THEREFOR AND APPLICATION THEREOF

(71) Applicants: SHANGHAI ADVANCED RESEARCH INSTITUTE, CHINESE ACADEMY OF SCIENCES, Shanghai (CN); SHANXI LUAN ENVIRONMENTAL ENERGY DEVELOPMENT CO., LTD., Changzhi (CN)

(72) Inventors: Zhengjia Li, Shanghai (CN); Liangshu Zhong, Shanghai (CN); Yuhan Sun, Shanghai (CN); Fei Yu, Shanghai (CN); Yunlei An, Shanghai (CN); Xingzhen Qi, Shanghai (CN); Tiejun Lin, Shanghai (CN); Yaning Xiao, Shanghai (CN); Bin Liu, Shanghai (CN); Dongfei Wang, Shanghai (CN)

(73) Assignees: SHANGHAI ADVANCED RESEARCH INSTITUTE, CHINESE ACADEMY OF SCIENCES, Shanghai (CN); SHANXI LUAN ENVIRONMENTAL ENERGY DEVELOPMENT CO., LTD., Changzhi (CN)

(*) Notice: Subject to any disclaimer, the term of this patent is extended or adjusted under 35 U.S.C. 154(b) by 371 days.

(21) Appl. No.: 16/090,586

(22) PCT Filed: Sep. 29, 2016

(86) PCT No.: PCT/CN2016/100772
§ 371 (c)(1),
(2) Date: Oct. 1, 2018

(87) PCT Pub. No.: WO2017/173791
PCT Pub. Date: Oct. 12, 2017

(65) Prior Publication Data
US 2020/0406239 A1    Dec. 31, 2020

(30) Foreign Application Priority Data
Apr. 6, 2016 (CN) .......................... 201610210920.5

(51) Int. Cl.
| | | |
|---|---|---|
| B01J 27/22 | (2006.01) | |
| C01B 32/914 | (2017.01) | |
| B01J 37/00 | (2006.01) | |
| B01J 37/02 | (2006.01) | |
| B01J 37/03 | (2006.01) | |
| B01J 37/04 | (2006.01) | |
| B01J 37/08 | (2006.01) | |
| B01J 37/18 | (2006.01) | |
| C07C 1/04 | (2006.01) | |

(52) U.S. Cl.
CPC ........... B01J 27/22 (2013.01); B01J 37/0018 (2013.01); B01J 37/0236 (2013.01); B01J 37/031 (2013.01); B01J 37/04 (2013.01); B01J 37/088 (2013.01); B01J 37/18 (2013.01); C01B 32/914 (2017.08); C07C 1/0435 (2013.01); C07C 2527/22 (2013.01)

(58) Field of Classification Search
CPC ....... C07C 11/02; C07C 1/04; C07C 2527/22; B01J 27/22; B01J 37/031; B01J 37/0018; B01J 37/04

See application file for complete search history.

(56) References Cited

U.S. PATENT DOCUMENTS

| | | |
|---|---|---|
| 6,509,382 B1 | 1/2003 | Ducreux et al. |
| 2015/0018438 A1* | 1/2015 | Ha .......................... C10G 2/334 518/716 |

FOREIGN PATENT DOCUMENTS

| | | |
|---|---|---|
| CN | 102770204 A | 11/2012 |
| CN | 105107523 A | 12/2015 |
| CN | 105772049 A | 7/2016 |

OTHER PUBLICATIONS

Hojlund et al., CA 1175796A, Oct. 9, 1984.*

* cited by examiner

*Primary Examiner* — Jafar F Parsa
(74) *Attorney, Agent, or Firm* — Global IP Services; Tianhua Gu

(57) ABSTRACT

A cobalt carbide-based catalyst for direct production of olefin from synthesis gas, a preparation method therefor and application thereof are disclosed. The method for preparing the catalyst comprises the following steps: 1) mixing a cobalt source with water, or mixing a cobalt source, an electron promoter and water to obtain a first solution; and mixing a precipitant with water to obtain a second solution; 2) adding the first solution and the second solution to water, or water and a structure promoter for precipitation, crystallizing, separating, drying and calcination; and 3) reducing a solid obtained in Step 2) in a reducing atmosphere, and then carbonizing in a carbonizing atmosphere. The prepared catalyst has high activity and high selectivity to olefins for direct production of olefins via syngas conversion.

2 Claims, 1 Drawing Sheet

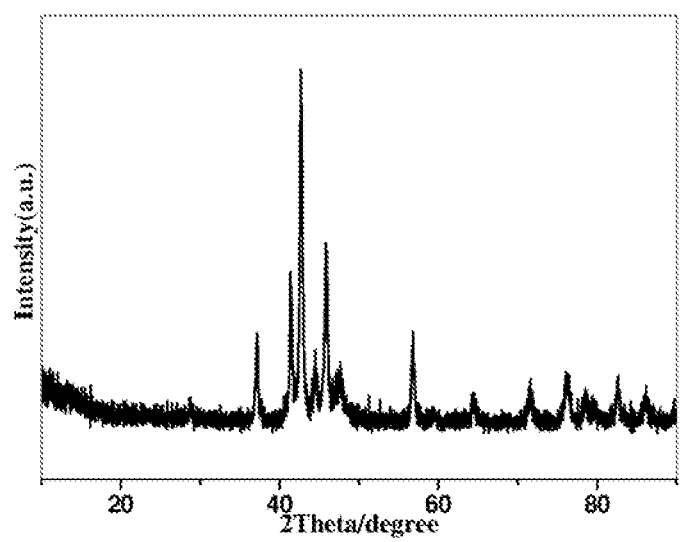

COBALT CARBIDE-BASED CATALYST FOR DIRECT PREPARATION OF OLEFIN FROM SYNTHESIS GAS, PREPARATION METHOD THEREFOR AND APPLICATION THEREOF

CROSS REFERENCE TO RELATED PATENT APPLICATION

The present application is the US national stage of PCT/CN2016/100772 filed on Sep. 29, 2016, which claims the priority of the Chinese patent application No. CN2016102109205 filed on Apr. 6, 2016, which application is incorporated herein by reference.

BACKGROUND OF THE PRESENT INVENTION

Field of Invention

The present invention relates to the technical field of catalyst technology, and particularly to a cobalt carbide-based catalyst for direct production of olefins from synthesis gas, a preparation method therefor, and application thereof.

Description of Related Arts

The production of olefins is one of the most important processes in petrochemical industry. Fischer-Tropsch (F-T) to olefins from synthesis gas (syngas, a mixture of hydrogen ($H_2$) and carbon monoxide (CO)) is a potential non-petroleum route and has received considerable attention.

The Fischer-Tropsch synthesis is a main route for the conversion and utilization of syngas. The existing Fischer-Tropsch synthesis process includes high-temperature Fischer-Tropsch synthesis and low-temperature Fischer-Tropsch synthesis. The high-temperature Fischer-Tropsch synthesis process developed by Sasol Limited (South Africa) is employed to produce mainly gasoline and low-molecular-weight linear chain alkanes by using a Fe-based catalyst in a fluidized bed reactor at a temperature ranging from 300 to 350° C. The low-temperature Fischer-Tropsch synthesis process is employed to produce mainly high-molecular-weight linear chain hydrocarbons by using a Fe-based or Co-based catalyst at a temperature ranging from 200 to 240° C. There are many factors affecting the catalytic performance, for example, the catalyst structure, reactor, and reaction conditions. As for the reaction conditions, the reaction temperature, reaction pressure, space velocity and gas composition may greatly affect the final catalytic performance. From a thermodynamic point of view, the reaction temperature mainly affects the chemical equilibrium of the reaction, and the increasing temperature is not necessarily favorable for the F-T synthesis reaction. When the temperature rises, the conversion of CO is accelerated. However, the carbon deposition reaction is an endothermic reaction, and increasing the temperature facilitates the occurrence of the carbon deposition. In addition, if the temperature is too high, the catalyst is susceptible to sintering, which will reduce the catalyst life and even damage the apparatus in a serious situation. In addition, from a kinetic point of view, with the increasing of the reaction rate as the temperature increases, and the side reaction rate also increases accordingly. Therefore, it is necessary to seek for a suitable reaction temperature which depends on the catalyst used. For the effect of pressure on the Fischer-Tropsch reaction, the researchers found that increasing the pressure generally speeds up the F-T synthesis reaction, but the side reaction rate also increases. Meanwhile, a too high pressure necessitates a high-pressure vessel, so that the investment cost of the equipment is high. In summary, in order to achieve an optimum Fischer-Tropsch catalytic performance, various influencing factors need to be optimized comprehensively.

A supported iron-based FTO catalyst has been reported by Krijn P. de Jong et al. (Science, 2012, 335, 835-838.). In the method, an iron species supported on an inert carbon nano tube carrier is used as a catalyst, wherein the interaction between the supporter and the active sites is weakened, thereby improving the selectivity to olefins. The selectivity to lower olefins is up to 61%, but the selectivity to methane is as high as 23%. In addition, the activity is rather low and the conversion is only about 1%. Yi Zhang et al. (ACS Catalysis, 2015, 5, 3905-3909) reported $Fe_3O_4$ microspheres with the surface modified with MnOx. Because only the FeCx active sites on the surface of the microspheres participate in the reaction, the influence of diffusion limitation is lowered. The catalyst has a selectivity to lower olefins of up to 60.1%, but the preparation method of the catalyst is cumbersome.

Bruce C. Gates et al. (J. Am. Chem. Soc., 1980, 102, 2478-2480.) reported that Co clusters are loaded in a type A molecular sieve cage by reduction with Cd gas and the products are found to be substantially propylene at 151° C. However, the Co cluster in the cage is extremely unstable. As the reaction proceeds, the Co cluster tends to migrate to the outside of the cage, agglomerates and grows, to finally exhibit the performance of a traditional Co-based catalyst for Fischer-Tropsch synthesis.

The FTO catalysts in the above literatures generally have the disadvantages of low selectivity to olefins and high selectivity to methane. Therefore, it is necessary to develop a new FTO catalyst having excellent performance, with which both the high selectivity to olefins and low selectivity to methane can be achieved.

SUMMARY OF THE PRESENT INVENTION

In order to overcome the disadvantages existing in the prior art, an object of the present invention is to provide a cobalt carbide-based catalyst for direct production of olefin from syngas, a preparation method therefor, and application thereof. The preparation method is simple, and the prepared catalyst possesses high activity and high selectivity to olefins.

The object of the present invention is accomplished through the following technical solutions.

In a first aspect of the present invention, a method for preparing a cobalt carbide-based catalyst for direct production of olefins from syngas is provided, which comprises the following steps:

1) mixing a cobalt source with water, or mixing a cobalt source, an electron promoter with water to obtain a first solution; and mixing a precipitant with water to obtain a second solution;

2) adding the first solution and the second solution to water, or water and a structure promoter for precipitation, crystallizing, separation, drying and calcination; and 3) reducing the solid obtained in Step 2) in a reducing atmosphere, and then carbonizing in a carbonizing atmosphere.

The separation may be separation by filtration or centrifugation.

Preferably, the method further comprises: adding an alkali metal promoter to the solid obtained in Step 3) by incipient wetness impregnation, then drying, and calcination, or adding an alkali metal promoter to the solid obtained in Step 2) by incipient wetness impregnation, then drying, calcination, and reducing in a reducing atmosphere.

Further preferably, the alkali metal promoter includes alkali metal hydroxide and/or alkali metal salt.

The alkali metal promoter may be an alkali metal hydroxide and/or an alkali metal salt well known in the art. The alkali metal hydroxide may be lithium hydroxide, sodium hydroxide, potassium hydroxide, rubidium hydroxide and cesium hydroxide. The alkali metal salt may be nitrate, carbonate, acetate, sulfate or chlorate.

Further preferably, one or more of the following are included:

1) the molar ratio of the cobalt source based on Co to the alkali metal promoter is 1:(0.001-0.5), and further preferably 1:(0.001-0.1), for example, 1:(0.001-0.01), 1:(0.01-0.1) or 1:(0.1-0.5);

2) the drying temperature is 60-120° C. and further preferably 60-100° C.; and the drying time is 4-48 hours, and further preferably 4-24 hours; and 3) the calcination temperature is 200-500° C. and further preferably 300-500° C.; and the calcination time is 1-24 hours, and further preferably 1-12 hours.

Preferably, one or more of the following are included:

1) the cobalt source is an organic cobalt source and/or an inorganic cobalt source;

2) the electron promoter is one or more selected from a transition metal salt, an alkaline earth metal salt, and a rare earth metal salt;

3) the precipitant is an alkali and/or a basic salt; and 4) the structure promoter is one or more selected from alumina, silica, titania, zirconia, magnesia and a carbon material.

The cobalt source may be any organic cobalt source and/or inorganic cobalt source well known in the art that can produce cobalt oxide. The organic cobalt source may be one or more of cobalt formate, cobalt acetate, and other organic cobalt sources. The inorganic cobalt source may be one or more of cobalt nitrate, cobalt chloride, cobalt sulfate, and other inorganic cobalt sources. Cobalt nitrate and/or cobalt chloride is further preferred.

The electron promoter may be one or more of a transition metal promoter, an alkaline earth metal promoter and a rare earth metal promoter well known in the art. The transition metal promoter may be one or more of vanadium, chromium, manganese, and other transition metals. The alkaline earth metal promoter may be one or more of beryllium, magnesium, calcium, strontium and barium. The rare earth metal promoter may be one or more of lanthanides, scandium and yttrium. One or more of manganese, lanthanide, and cerium are further preferred.

The precipitant may be an alkali and/or a basic salt well known in the art. The alkali may be one or more of lithium hydroxide, sodium hydroxide, potassium hydroxide, aqueous ammonia, and other bases. The basic salt may be one or more of sodium carbonate, ammonium carbonate, sodium bicarbonate, potassium carbonate, and other basic salts. Sodium carbonate and/or ammonium carbonate is/are further preferred.

The structure promoter may be one or more carriers well known in the art. The carrier may be one or more of alumina, silica, titania, zirconia, magnesia, a carbon material, and other carriers. The carbon material and/or zirconia is/are further preferred.

Preferably, any one or more of the following are included:

1) In Step 1), the molar ratio of the cobalt source (based on Co):electron promoter:water is 1:(0-10):(1-1000), more preferably 1:(0-5):(1-1000), further preferably 1:(0-5):(25-1000), and still further preferably 1:(0-2):(25-500). For example, the molar ratio of the cobalt source:electron promoter is 1:(0-0.1), 1:(0.1-0.2), 1:(0.2-0.3), 1:(0.3-0.5), 1:(0.5-1), 1:(1-2), 1:(2-5) or 1:(5-10), and the molar ratio of the cobalt source:water is 1:(1-25), 1:(25-35), 1:(35-40), 1:(40-50), 1:(50-60), 1:(60-100), 1:(100-500) or 1:(500-1000).

2) In Step 1), the molar ratio of the precipitant to water is 1:1-1000 and further preferably 1:(25-800), for example, 1:(1-25), 1:(25-30), 1:(30-50), 1:(50-75), 1:(75-100), 1:(100-200), 1:(200-500), 1:(500-800) or 1:(800-1000).

3) In Step 2), when the first solution and the second solution are added to water, the weight ratio of cobalt:water is 1:(1-1000), for example, 1:(1-10), 1:(10-20), 1:(20-50), 1:(50-80), 1:(80-100), 1:(100-110), 1:(110-150), 1:(150-250), 1:(250-500), 1:(500-800), 1:(800-900) or 1:(900-1000).

4) In Step 2), when the first solution and the second solution are added to water and the structure promoter, the weight ratio of the structure promoter:cobalt:water is 1:(0.05-1):(1-1000), and further preferably 1:(0.1-0.5):(10-1000). For example, the weight ratio of the structure promoter:cobalt is 1:(0.05-0.1), 1:(0.1-0.2), 1:(0.2-0.3), 1:(0.3-0.4), 1:(0.4-0.5), 1:(0.5-0.8) or 1:(0.8-1); and the weight ratio of the structure promoter:water is 1:(10-100), 1:(100-500), 1:(500-800) or 1:(800-1000). The water in the weight ratio refers to the water added in Step 2).

Preferably, one or more of the following are included:

1) In Step 2), the precipitation temperature is 0-90° C., and further preferably 0-80° C.; and the pH is controlled to 7-12, and further preferably 7-10. For example, the precipitation temperature is 0-15° C., 15-20° C., 20-25° C., 25-30° C., 30-50° C., 50-60° C., 60-80° C. or 80-90° C., and the pH is controlled to 7-7.5, 7.5-8, 8-9, 9-10 or 10-12.

2) In Step 2), the crystallization temperature is 0-200° C., preferably 30-180° C.; and the crystallization time is 1-72 hours, and further preferably 2-48 hours. For example, the crystallization temperature is 0-30° C., 30-60° C., 60-70° C., 70-80° C., 80-100° C., 100-120° C., 120-150° C., 150-180° C. or 180-200° C.; and the crystallization time is 1-2 hours, 2-4 hours, 4-5 hours, 5-6 hours, 6-10 hours, 10-12 hours, 12-48 hours or 48-72 hours.

3) In Step 2), the drying temperature is 60-120° C., preferably 60-100° C.; and the drying time is 4-48 hours, and further preferably 4-24 hours. For example, the drying temperature is 60-80° C., 80-100° C. or 100-120° C., and the drying time is 4-10 hours, 10-12 hours, 12-24 hours, or 24-48 hours.

4) In Step 2), the calcination temperature is 200-500° C., preferably 300-500° C.; and the calcination time is 1-24 hours, and further preferably 1-12 hours. For example, the calcination temperature is 200-300° C., 300-330° C., 330-400° C. or 400-500° C., and the calcination time is 1-3 hours, 3-4 hours, 4-5 hours, 5-6 hours, 6-12 hours or 12-24 hours.

5) In Step 3), the reduction conditions are as follows. The reduction temperature is 100-600° C., preferably 300-500° C.; the reduction pressure is 0.1-10 MPa, and further preferably 0.1-1 MPa; the gas hourly space velocity is 500-100,000 $h^{-1}$, and preferably 2000-10000 $h^{-1}$; the reduction time is 1-24 hours, and further preferably 1-12 hours. For example, the reduction temperature is 100-250° C., 250-300° C., 300-400° C., 400-500° C. or 500-600° C.; the reduction pressure is 0.1-0.7 MPa, 0.7-0.8 MPa, 0.8-1 MPa, 1-2 MPa, 2-3 MPa, 3-5 MPa, 5-6 MPa, 6-7 MPa, 7-8 MPa or 8-10 MPa; the gas hourly space velocity is 500-2000 $h^{-1}$, 2000-4000 h$^{-1}$, 4000-5000 h$^{-1}$, 5000-8000 h$^{-1}$, 8000-10000 h$^{-1}$; and the reduction time is 1-4 hours, 4-5 hours, 5-8 hours, 8-12 hours or 12-24 hours.

6) In Step 3), the conditions are as follows. The carbonization temperature is 100-500° C., and further preferably 150-300° C.; the carbonization pressure is 0.1-10 MPa, and further preferably 0.1-1 MPa; the gas hourly space velocity is 500-100,000 h$^{-1}$, and further preferably 2000-10000 h$^{-1}$; the carbonization time is 1-72 hours, and further preferably 1-48 hours. For example, the carbonization temperature is 100-150° C., 150-200° C., 200-250° C., 250-300° C., 300-320° C., 320-350° C., 350-400° C. or 400-500° C.; the carbonization pressure is 0.1-0.2 MPa, 0.2-0.5 MPa, 0.5-0.9 MPa, 0.9-1 MPa, 1-2 MPa, 2-4 MPa, 4-5 MPa, 5-7 MPa, 7-8 MPa or 8-10 MPa; the gas hourly space velocity is 500-2000 h$^{-1}$, 2000-8000 h$^{-1}$, 8000-10,000 h$^{-1}$, 10000-20,000 h$^{-1}$ or 20000-100,000 h$^{-1}$; and the time is 1-4 hours, 4-6 hours, 6-8 hours, 8-12 hours, 12-18 hours, 18-24 hours, 24-48 hours or 48-72 hours.

In Step 3), the reducing atmosphere may be one or more of the reducing gases known in the art. Preferably, in Step 3), the reducing atmosphere is hydrogen, carbon monoxide, a mixture of hydrogen or carbon monoxide with an inert gas at any ratio. Further preferably, the reducing atmosphere is hydrogen and/or a mixture of 10% hydrogen/argon.

In Step 3), the carbonizing atmosphere may be one or more of the carbonizing carburizing atmospheres known in the art. Preferably, in Step 3), the atmosphere is carbon monoxide, or a mixture of carbon monoxide and other gases, where the other gases may be hydrogen and/or inert gases. Carbon monoxide and/or syngas is/are further preferred.

In a second aspect of the present invention, a cobalt carbide-based catalyst for direct production of olefin from syngas is provided, which is prepared through the above method.

In a third aspect of the present invention, use of the cobalt carbide-based catalyst for direct production of olefin from syngas in the direct production of olefin is provided. The reaction conditions are as follows. The reaction temperature is 150-500° C., and preferably 200° C.-300° C.; the reaction pressure is 0.1-10 MPa, and preferably 0.1-1 MPa; the gas hourly space velocity is 500-100,000 h$^{-1}$, and preferably 1000-40,000 h$^{-1}$, and the molar ratio of H$_2$ to CO is 1:10-10:1, and preferably 1:3-3:1. For example, the reaction temperature is 150-200° C., 200-230° C., 230-240° C., 240-250° C., 250-260° C., 260-270° C., 270-300° C. or 300-500° C.; the reaction pressure is 0.1-0.5 MPa, 0.5-1 MPa or 1-10 MPa; the gas hourly space velocity is 500-1000 h$^{-1}$, 1000-2000 h$^{-1}$, 2000-4000 h$^{-1}$ or 4000-100,000 h$^{-1}$; and the molar ratio of H$_2$ to CO is 1:10-1:3, 1:3-2:1, 2:1-3:1 or 3:1-10:1.

Preferably, the reaction is carried out in a fixed bed, a slurry bed or a fluidized bed. Further preferably, the reaction is carried out in a fixed bed.

In the above technical solution, the precipitation method is a method known to those skilled in the art. For example, a double drop method or a single drop method may be carried out at a certain dropping temperature at a certain temperature and pH.

In the above technical solution, the crystallization method is a method known to those skilled in the art. For example, the crystallization is continued with stirring or hydrothermally for a period of time at a certain temperature.

In the above technical solution, the drying method is a method known to those skilled in the art. For example, the drying is continued for a period of time at a certain temperature. The drying may take place under vacuum, in an air atmosphere, or in an inert atmosphere.

In the above technical solution, the calcination method is a method known to those skilled in the art. For example, the calcination is continued for a period of time at a certain temperature. The calcination may take place under vacuum, in an air atmosphere, or in an inert atmosphere.

In the above technical solution, the reduction method is a method known to those skilled in the art. For example, the reduction is continued for a period of time at a certain temperature and gas hourly space velocity in a reducing atmosphere.

In the above technical solution, the carbonization method is a method known to those skilled in the art. For example, the carbonization is continued for a period of time at a certain temperature and gas hourly space velocity in a carbonizing atmosphere.

In the above technical solution, the incipient wetness impregnation method is a method known to those skilled in the art. For example, a solution is formulated according to a certain ratio, drying is continued for a period of time at a certain temperature, and calcination is continued for a period of time at a certain temperature. The drying may take place under vacuum, in an air atmosphere, or in an inert atmosphere. The calcination may take place under vacuum, in an air atmosphere, or in an inert atmosphere.

In the method for preparing a cobalt carbide-based catalyst for direct production of olefin from syngas according to the present invention, a cobalt source that is an active center and an electron promoter are mixed and dissolved to form a mixed solution, and then precipitated on a carrier with the aid of a precipitant solution, by accurately controlling the temperature and the pH at which the precipitation occurs; and then the prepared catalyst is subjected to low-temperature reduction and carbonization treatment. The obtained cobalt carbide-based catalyst has a high selectivity to olefins, a low selectivity to methane and a high catalytic activity.

BRIEF DESCRIPTION OF THE DRAWINGS

FIG. 1 describes the X-ray diffraction pattern of a catalyst obtained in Example 1, showing that the active phase is Co$_2$C.

DETAILED DESCRIPTION OF THE PREFERRED EMBODIMENTS

The technical solutions of the present invention are explained below by way of specific examples. It should be understood that the one or more method steps mentioned in the present invention does not exclude a situation that there are other method steps before or after the combination of steps or other steps may be inserted between these explicitly mentioned steps. It should also be understood that these examples are merely illustrative of the present invention and are not intended to limit the scope of the present invention. Moreover, unless otherwise stated, the numbering of each method step is merely a convenient tool for identifying the each method step, and is not intended to limit the order in which the method steps are arranged, or to limit the scope of the present invention. The change or adjustment made to the relative relationship thereof without substantially change the technical content is also deemed to fall within the scope of the present invention.

The technical details of the present invention are elaborated by the following examples. It is to be noted that the examples are merely illustrative of the technical features of the present invention and are not intended to limit the present invention.

Example 1

Cobalt nitrate was fully dissolved in water by stirring at a molar ratio of cobalt nitrate:water=1:25, to obtain a first solution. Sodium carbonate was fully dissolved in water by stirring at a molar ratio of sodium carbonate:water=1:25, to obtain a second solution. A certain amount of deionized water is prepared according to a weight ratio of cobalt:water=1:10. Both the first solution and the second solution were added dropwise to the deionized water at a precipitation temperature of 60° C. and pH controlled to 8. After addition, it was crystallized at a temperature of 60° C. for 2 hours, and centrifuged. The obtained solid product was dried at 80° C. for 12 hours, and the dried solid was calcined at 330° C. for 4 hours. The solid was reduced for 4 hours at 250° C. under a pure $H_2$ atmosphere of 0.1 MPa at a space velocity of 8000 $h^{-1}$, and then carbonized for 6 hours at 250° C. under a CO atmosphere of 0.1 MPa at a space velocity of 8000 $h^{-1}$. FIG. 1 shows an X-ray diffraction pattern. Reaction was carried out with syngas of $H_2/CO=2$ as a raw gas at 240° C., under 0.1 MPa, and at a space velocity of 2000 $h^{-1}$. The experimental results are shown in Table 1.

Example 2

Cobalt nitrate and manganese nitrate were fully dissolved in water by stirring at a molar ratio of cobalt nitrate:manganese nitrate:water=1:5:25, to obtain a first solution. Sodium carbonate was fully dissolved in water by stirring at a molar ratio of sodium carbonate:water=1:25, to obtain a second solution. A certain amount of deionized water is prepared according to a weight ratio of cobalt:water=1:100. Both the first solution and the second solution were added dropwise to the deionized water at a precipitation temperature of 30° C. and pH controlled to 8. After addition, it was crystallized at a temperature of 30° C. for 4 hours, and centrifuged. The obtained solid product was dried at 80° C. for 10 hours, and the dried solid was calcined at 330° C. for 3 hours. The solid was reduced for 5 hours at 300° C. under a 10% $H_2/Ar$ atmosphere of 1 MPa at a space velocity of 8000 $h^{-1}$, and then carbonized for 8 hours at 250° C. under a CO atmosphere of 0.1 MPa at a space velocity of 8000 $h^{-1}$. Reaction was carried out with syngas of $H_2/CO=10$ as a raw gas at 260° C., under 0.1 MPa, and at a space velocity of 2000 $h^{-1}$. The experimental results are shown in Table 1.

Example 3

Cobalt acetate was fully dissolved in water by stirring at a molar ratio of cobalt acetate:water=1:25, to obtain a first solution. Sodium carbonate was fully dissolved in water by stirring at a molar ratio of sodium carbonate:water=1:1000, to obtain a second solution. A certain amount of deionized water is prepared according to a weight ratio of cobalt:water=1:20. Both the first solution and the second solution were added dropwise to the deionized water at a precipitation temperature of 60° C. and pH controlled to 8. After addition, it was crystallized at a temperature of 180° C. for 2 hours, and centrifuged. The obtained solid product was dried at 80° C. for 12 hours, and the dried solid was calcined at 330° C. for 4 hours. The solid was reduced for 4 hours at 250° C. under a pure $H_2$ atmosphere of 10 MPa at a space velocity of 10000 $h^{-1}$, and then carbonized for 6 hours at 250° C. under a CO atmosphere of 0.1 MPa at a space velocity of 8000 $h^{-1}$. Reaction was carried out with syngas of $H_2/CO=0.1$ as a raw gas at 240° C., under 0.1 MPa, and at a space velocity of 2000 $h^{-1}$. The experimental results are shown in Table 1.

Example 4

Cobalt formate was fully dissolved in water by stirring at a molar ratio of cobalt formate:water=1:50, to obtain a first solution. Sodium carbonate was fully dissolved in water by stirring at a molar ratio of sodium carbonate:water=1:500, to obtain a second solution. A certain amount of deionized water is prepared according to a weight ratio of cobalt:water=1:1000. Both the first solution and the second solution were added dropwise to the deionized water at a precipitation temperature of 60° C. and pH controlled to 8. After addition, it was crystallized at a temperature of 60° C. for 2 hours, and centrifuged. The obtained solid product was dried at 80° C. for 12 hours, and the dried solid was calcined at 330° C. for 4 hours. The solid was reduced for 4 hours at 250° C. under a pure $H_2$ atmosphere of 0.1 MPa at a space velocity of 8000 $h^{-1}$, and then carbonized for 6 hours at 250° C. under a CO atmosphere of 10 MPa at a space velocity of 10000 $h^{-1}$. Reaction was carried out with syngas of $H_2/CO=1:3$ as a raw gas at 240° C., under 0.1 MPa, and at a space velocity of 2000 $h^{-1}$. The experimental results are shown in Table 1.

Example 5

Cobalt nitrate was fully dissolved in water by stirring at a molar ratio of cobalt nitrate:water=1:25, to obtain a first solution. Potassium hydroxide was fully dissolved in water by stirring at a molar ratio of potassium hydroxide:water=1:1, to obtain a second solution. A certain amount of deionized water is prepared according to a weight ratio of cobalt:water=1:500. Both the first solution and the second solution were added dropwise to the deionized water at a precipitation temperature of 60° C. and pH controlled to 8. After addition, it was crystallized at a temperature of 60° C. for 2 hours, and centrifuged. The obtained solid product was dried at 80° C. for 12 hours, and the dried solid was calcined at 330° C. for 4 hours. The solid was reduced for 4 hours at 250° C. under a pure $H_2$ atmosphere of 0.1 MPa at a space velocity of 8000 $h^{-1}$, and then carbonized for 6 hours at 250° C. under a CO atmosphere of 5 MPa at a space velocity of 8000 $h^{-1}$. Reaction was carried out with syngas of $H_2/CO=3$ as a raw gas at 240° C., under 0.1 MPa, and at a space velocity of 2000 $h^{-1}$. The experimental results are shown in Table 1.

Example 6

Cobalt nitrate was fully dissolved in water by stirring at a molar ratio of cobalt nitrate:water=1:50 AM, to obtain a first solution. Sodium hydroxide was fully dissolved in water by stirring at a molar ratio of sodium hydroxide:water=1:75, to obtain a second solution. A certain amount of deionized water is prepared according to a weight ratio of cobalt:water=1:50. Both the first solution and the second solution were added dropwise to the deionized water at a precipitation temperature of 60° C. and pH controlled to 8. After addition, it was crystallized at a temperature of 60° C. for 2 hours, and centrifuged. The obtained solid product was dried at 80° C. for 12 hours, and the dried solid was calcined at 330° C. for 5 hours. The solid was reduced for 4 hours at 250° C. under a pure $H_2$ atmosphere of 5 MPa at a space velocity of 8000 $h^{-1}$, and then carbonized for 4 hours at 250° C. under a CO atmosphere of 0.1 MPa at a space velocity of 8000 $h^{-1}$. Reaction was carried out with syngas of $H_2/CO=2$ as a raw gas at 250° C., under 0.1 MPa, and at a space velocity of 40000 $h^{-1}$. The experimental results are shown in Table 1.

Example 7

Cobalt nitrate was fully dissolved in water by stirring at a molar ratio of cobalt nitrate:water=1:50 AM, to obtain a first solution. Ammonium carbonate was fully dissolved in water by stirring at a molar ratio of ammonium carbonate:water=1:100, to obtain a second solution. A certain amount of deionized water is prepared according to a weight ratio of cobalt:water=1:900. Both the first solution and the second solution were added dropwise to deionized water at a precipitation temperature of 80° C. and a pH controlled to 8. After addition, it was crystallized at a temperature of 60° C. for 2 hours, and centrifuged. The obtained solid product was dried at 80° C. for 12 hours, and the dried solid was calcined at 330° C. for 5 hours. The solid was reduced for 4 hours at 250° C. under a pure $H_2$ atmosphere of 1 MPa at a space velocity of 8000 $h^{-1}$, and then carbonized for 12 hours at 250° C. under a CO atmosphere of 1 MPa at a space velocity of 8000 $h^{-1}$. Reaction was carried out with syngas of $H_2/CO=2$ as a raw gas at 230° C., under 0.1 MPa, and at a space velocity of 500 $h^{-1}$. The experimental results are shown in Table 1.

Example 8

Cobalt nitrate was fully dissolved in water by stirring at a molar ratio of cobalt nitrate:water=1:50 AM, to obtain a first solution. Sodium bicarbonate was fully dissolved in water by stirring at a molar ratio of sodium bicarbonate:water=1:50, to obtain a second solution. A certain amount of deionized water is prepared according to a weight ratio of cobalt:water=1:80. Both the first solution and the second solution were added dropwise to deionized water at a precipitation temperature of 80° C. and pH controlled to 9. After addition, it was crystallized at a temperature of 60° C. for 2 hours, and centrifuged. The obtained solid product was dried at 80° C. for 12 hours, and the dried solid was calcined at 330° C. for 5 hours. The solid was reduced for 4 hours at 250° C. under a pure $H_2$ atmosphere of 0.1 MPa at a space velocity of 8000 $h^{-1}$, and then carbonized for 6 hours at 300° C. under a CO atmosphere of 10 MPa at a space velocity of 8000 $h^{-1}$. Reaction was carried out with syngas of $H_2/CO=2$ as a raw gas at 250° C., under 0.1 MPa, and at a space velocity of 1000 $h^{-1}$. The experimental results are shown in Table 1.

Example 9

Cobalt nitrate and lanthanum nitrate were fully dissolved in water by stirring at a molar ratio of cobalt nitrate:lanthanum nitrate:water=1:0.5:25, to obtain a first solution. Sodium carbonate was fully dissolved in water by stirring at a molar ratio of sodium carbonate:water=1:50, to obtain a second solution. A certain amount of deionized water is prepared according to a weight ratio of cobalt:water=1:10. Both the first solution and the second solution were added dropwise to the deionized water at a precipitation temperature of 20° C. and a pH controlled to 7.5. After addition, it was crystallized at a temperature of 60° C. for 4 hours, and centrifuged. The obtained solid product was dried at 80° C. for 10 hours, and the dried solid was calcined at 330° C. for 3 hours. The solid was reduced for 5 hours at 500° C. under a 10% $H_2/Ar$ atmosphere of 1 MPa at a space velocity of 8000 $h^{-1}$, and then carbonized for 6 hours at 350° C. under a CO atmosphere of 2 MPa at a space velocity of 8000 $h^{-1}$. Reaction was carried out with syngas of $H_2/CO=2$ as a raw gas at 270° C., under 0.1 MPa, and at a space velocity of 100000 $h^{-1}$. The experimental results are shown in Table 1.

Example 10

Cobalt nitrate and cerium nitrate were fully dissolved in water by stirring at a molar ratio of cobalt nitrate:cerium nitrate:water=1:0.3:25, to obtain a first solution. Sodium carbonate was fully dissolved in water by stirring at a molar ratio of sodium carbonate:water=1:800, to obtain a second solution. A certain amount of deionized water is prepared according to a weight ratio of cobalt:water=1:110. Both the first solution and the second solution were added dropwise to the deionized water at a precipitation temperature of 30° C. and pH controlled to 8. After addition, it was crystallized at a temperature of 60° C. for 4 hours, and centrifuged. The obtained solid product was dried at 80° C. for 10 hours, and the dried solid was calcined at 330° C. for 4 hours. The solid was reduced for 5 hours at 300° C. under a 10% $H_2/Ar$ atmosphere of 3 MPa at a space velocity of 500 $h^{-1}$, and then carbonized for 12 hours at 350° C. under a CO atmosphere of 8 MPa at a space velocity of 8000 $h^{-1}$. Reaction was carried out with syngas of $H_2/CO=2$ as a raw gas at 260° C., under 10 MPa, and at a space velocity of 2000 $h^{-1}$. The experimental results are shown in Table 1.

Example 11

Cobalt nitrate and ammonium meta-vanadate were fully dissolved in water by stirring at a molar ratio of cobalt nitrate:ammonium meta-vanadate:water=1:0.1:1000, to obtain a first solution. Sodium carbonate was fully dissolved in water by stirring at a molar ratio of sodium carbonate:water=1:1000, to obtain a second solution. A certain amount of deionized water is prepared according to a weight ratio of cobalt:water=1:100. Both the first solution and the second solution were added dropwise to the deionized water at a precipitation temperature of 20° C. and pH controlled to 8. After addition, it was crystallized at a temperature of 60° C. for 2 hours, and centrifuged. The obtained solid product was dried at 80° C. for 10 hours, and the dried solid was calcined at 330° C. for 4 hours. The solid was reduced for 1 hour at 300° C. under a 10% $H_2/Ar$ atmosphere of 8 MPa at a space velocity of 8000 $h^{-1}$, and then carbonized for 12 hours at 300° C. under a CO atmosphere of 0.1 MPa at a space velocity of 8000 $h^{-1}$. Reaction was carried out with syngas of $H_2/CO=2$ as a raw gas at 150° C., under 0.1 MPa, and at a space velocity of 2000 $h^{-1}$. The experimental results are shown in Table 1.

Example 12

Cobalt nitrate and potassium chromate were fully dissolved in water by stirring at a molar ratio of cobalt nitrate:potassium chromate:water=1:0.3:1, to obtain a first solution. Sodium carbonate was fully dissolved in water by stirring at a molar ratio of sodium carbonate:water=1:50, to obtain a second solution. A certain amount of deionized water is prepared according to a weight ratio of cobalt:water=1:50. Both the first solution and the second solution were added dropwise to the deionized water at a precipitation temperature of 30° C. and pH controlled to 8. After addition, it was crystallized at a temperature of 60° C. for 5 hours, and centrifuged. The obtained solid product was dried at 80° C. for 10 hours, and the dried solid was calcined at 330° C. for 5 hours. The solid was reduced for 24 hours at 100° C. under a 10% $H_2$/Ar atmosphere of 5 MPa at a space velocity of 8000 $h^{-1}$, and then carbonized for 6 hours at 400° C. under a CO atmosphere of 7 MPa at a space velocity of 8000 $h^{-1}$. Reaction was carried out with syngas of $H_2$/CO=2 as a raw gas at 240° C., under 0.1 MPa, and at a space velocity of 2000 $h^{-1}$. The experimental results are shown in Table 1.

Example 13

Cobalt nitrate and lanthanum nitrate were fully dissolved in water by stirring at a molar ratio of cobalt nitrate: lanthanum nitrate:water=1:10:100, to obtain a first solution. Sodium carbonate was fully dissolved in water by stirring at a molar ratio of sodium carbonate:water=1:50 AM, to obtain a second solution. A certain amount of deionized water is prepared according to a weight ratio of cobalt:water=1:100. Both the first solution and the second solution were added dropwise to the deionized water at a precipitation temperature of 15° C. and a pH controlled to 7.5. After addition, it was crystallized at a temperature of 70° C. for 6 hours, and centrifuged. The obtained solid product was dried at 80° C. for 10 hours, and the dried solid was calcined at 300° C. for 5 hours. The solid was reduced for 5 hours at 600° C. under a $H_2$ atmosphere of 0.1 MPa at a space velocity of 8000 $h^{-1}$, and then carbonized for 6 hours at 250° C. under a 10% CO/He atmosphere of 7 MPa at a space velocity of 8000 $h^{-1}$. Reaction was carried out with syngas of $H_2$/CO=2 as a raw gas at 500° C., under 0.1 MPa, and at a space velocity of 2000 $h^{-1}$. The experimental results are shown in Table 1.

Example 14

Cobalt nitrate and magnesium chloride were fully dissolved in water by stirring at a molar ratio of cobalt nitrate:magnesium chloride:water=1:0.2:100, to obtain a first solution. Sodium carbonate was fully dissolved in water by stirring at a molar ratio of sodium carbonate:water=1:50, to obtain a second solution. A certain amount of deionized water is prepared according to a weight ratio of cobalt:water=1:80. Both the first solution and the second solution were added dropwise to the deionized water at a precipitation temperature of 25° C. and pH controlled to 9. After addition, it was crystallized at a temperature of 70° C. for 6 hours, and centrifuged. The obtained solid product was dried at 80° C. for 10 hours, and the dried solid was calcined at 300° C. for 5 hours. The solid was reduced for 5 hours at 300° C. under a $H_2$ atmosphere of 10 MPa at a space velocity of 8000 $h^{-1}$, and then carbonized for 72 hours at 300° C. under a 10% CO/He atmosphere of 0.1 MPa at a space velocity of 500 $h^{-1}$. Reaction was carried out with syngas of $H_2$/CO=2 as a raw gas at 260° C., under 0.1 MPa, and at a space velocity of 2000 $h^{-1}$. The experimental results are shown in Table 1.

Example 15

1) Cobalt acetate and cerium nitrate were fully dissolved in water by stirring at a molar ratio of cobalt acetate:cerium nitrate:water=1:5:50, to obtain a first solution. Ammonium carbonate was fully dissolved in water by stirring at a molar ratio of ammonium carbonate:water=1:100, to obtain a second solution. 2) Zirconia was stirred uniformly in water according to a weight ratio of zirconia:cobalt:water=1:0.05:10. Both the first solution and the second solution obtained in Step 1) were added dropwise to the solution obtained in Step 2) at a precipitation temperature of 90° C. and pH controlled to 9. After addition, it was crystallized at a temperature of 150° C. for 72 hours, and filtered or centrifuged. The obtained solid product was dried at 80° C. for 48 hours, and then calcined at 500° C. for 4 hours. The solid was reduced for 5 hours at 300° C. under a pure $H_2$ atmosphere of 10 MPa at a space velocity of 4000 $h^{-1}$, and then carbonized for 12 hours at 250° C. under a 10% CO/He atmosphere of 10 MPa at a space velocity of 8000 $h^{-1}$. Reaction was carried out with syngas of $H_2$/CO=2 as a raw gas at 270° C., under 0.1 MPa, and at a space velocity of 2000 $h^{-1}$. The experimental results are shown in Table 1.

Example 16

1) Cobalt chloride and lanthanum nitrate were fully dissolved in water by stirring at a molar ratio of cobalt chloride:lanthanum nitrate:water=1:2:100, to obtain a first solution. Potassium carbonate was fully dissolved in water by stirring at a molar ratio of potassium carbonate:water=1:50, to obtain a second solution. 2) Activated carbon was stirred uniformly in water according to a weight ratio of carbon:cobalt:water=1:0.3:1000. Both the first solution and the second solution obtained in Step 1) were added dropwise to the solution obtained in Step 2) at a precipitation temperature of 50° C. and a pH controlled to 7.5. After addition, it was crystallized at a temperature of 100° C. for 10 hours, and centrifuged. The obtained solid product was dried at 120° C. for 48 hours, and the dried solid was calcined at 300° C. for 4 hours. The solid was reduced for 5 hours at 300° C. under a 10% $H_2$/Ar atmosphere of 6 MPa at a space velocity of 8000 $h^{-1}$, and then carbonized for 1 hour at 100° C. under a 10% CO/He atmosphere of 0.1 MPa at a space velocity of 2000 $h^{-1}$. Reaction was carried out with syngas of $H_2$/CO=2 as a raw gas at 240° C., under 0.1 MPa, and at a space velocity of 2000 $h^{-1}$. The experimental results are shown in Table 1.

Example 17

1) Cobalt nitrate and magnesium nitrate were fully dissolved in water by stirring at a molar ratio of cobalt nitrate:magnesium nitrate:water=1:1:50, to obtain a first solution. Ammonium carbonate was fully dissolved in water by stirring at a molar ratio of ammonium carbonate:water=1:100, to obtain a second solution. 2) Silica was stirred uniformly in water according to a weight ratio of silica:cobalt:water=1:1:1. Both the first solution and the second solution obtained in Step 1) were added dropwise to the solution obtained in Step 2) at a precipitation temperature of 0° C. and pH controlled to 7. After addition, it was crystallized at a temperature of 120° C. for 12 hours, and filtered or centrifuged. The obtained solid product was dried at 80° C. for 24 hours, and then calcined at 400° C. for 6 hours. The solid was reduced for 12 hours at 400° C. under a pure $H_2$ atmosphere of 2 MPa at a space velocity of 2000 $h^{-1}$, and then carbonized for 6 hours at 500° C. under a 10% CO/He atmosphere of 2 MPa at a space velocity of 2000 $h^{-1}$. Reaction was carried out with syngas of $H_2$/CO=2 as a raw gas at 300° C., under 0.1 MPa, and at a space velocity of 2000 $h^{-1}$. The experimental results are shown in Table 1.

Example 18

1) Cobalt acetate was fully dissolved in water by stirring at a molar ratio of cobalt acetate:water=1:25, to obtain a first solution. Potassium hydroxide was fully dissolved in water by stirring at a molar ratio of potassium hydroxide:water=1:25, to obtain a second solution. 2) Titania was stirred uniformly in water according to a weight ratio of titania:cobalt:water=1:0.4:800. Both the first solution and the second solution obtained in Step 1) were added dropwise to the solution obtained in Step 2) at a precipitation temperature of 90° C. and pH controlled to 10. After addition, it was crystallized at a temperature of 80° C. for 72 hours, and centrifuged. The obtained solid product was dried at 60° C. for 48 hours, and the dried solid was calcined at 330° C. for 12 hours. The solid was reduced for 8 hours at 400° C. under a 10% $H_2$/Ar atmosphere of 0.1 MPa at a space velocity of 8000 $h^{-1}$, and then carbonized for 6 hours at 250° C. under a 10% CO/He atmosphere of 2 MPa at a space velocity of 100,000 $h^{-1}$. Reaction was carried out with syngas of $H_2$/CO=2 as a raw gas at 200° C., under 0.1 MPa, and at a space velocity of 2000 $h^{-1}$. The experimental results are shown in Table 1.

Example 19

1) Cobalt nitrate was fully dissolved in water by stirring at a molar ratio of cobalt nitrate:water=1:35, to obtain a first solution. Potassium carbonate was fully dissolved in water by stirring at a molar ratio of potassium carbonate:water=1:25, to obtain a second solution. 2) Alumina was stirred uniformly in water according to a weight ratio of alumina:cobalt:water=1:0.8:1000. Both the first solution and the second solution obtained in Step 1) were added dropwise to the solution obtained in Step 2) at a precipitation temperature of 90° C. and pH controlled to 9. After addition, it was crystallized at a temperature of 80° C. for 72 hours, and centrifuged. The obtained solid product was dried at 80° C. for 48 hours, and the dried solid was calcined at 330° C. for 12 hours. The solid was reduced for 8 hours at 400° C. under a 10% CO/Ar atmosphere of 0.1 MPa at a space velocity of 8000 $h^{-1}$, and then carbonized for 18 hours at 320° C. under a 10% CO/He atmosphere of 5 MPa at a space velocity of 8000 $h^{-1}$. Reaction was carried out with syngas of $H_2$/CO=2 as a raw gas at 200° C., under 0.1 MPa, and at a space velocity of 2000 $h^{-1}$. The experimental results are shown in Table 1.

Example 20

1) Cobalt nitrate was fully dissolved in water by stirring at a molar ratio of cobalt nitrate:water=1:40, to obtain a first solution. Potassium carbonate was fully dissolved in water by stirring at a molar ratio of potassium carbonate:water=1:30, to obtain a second solution. 2) Alumina was stirred uniformly in water according to a weight ratio of alumina:cobalt:water=1:1:500. Both the first solution and the second solution obtained in Step 1) were added dropwise to the solution obtained in Step 2) at a precipitation temperature of 90° C. and a pH controlled to 9. After addition, it was crystallized at a temperature of 80° C. for 72 hours, and centrifuged. The obtained solid product was dried at 80° C. for 48 hours, and the dried solid was calcined at 330° C. for 12 hours. The solid was reduced for 8 hours at 400° C. under a 10% CO/Ar atmosphere of 0.1 MPa at a space velocity of 8000 $h^{-1}$, and then carbonized for 24 hours at 300° C. under a 10% CO/He atmosphere of 10 MPa at a space velocity of 8000 $h^{-1}$. Reaction was carried out with syngas of $H_2$/CO=2 as a raw gas at 200° C., under 0.1 MPa, and at a space velocity of 2000 $h^{-1}$. The experimental results are shown in Table 1.

Example 21

Cobalt nitrate and manganese nitrate were fully dissolved in water by stirring at a molar ratio of cobalt nitrate:manganese nitrate:water=1:0.5:25, to obtain a first solution. Sodium carbonate was fully dissolved in water by stirring at a molar ratio of sodium carbonate:water=1:25, to obtain a second solution. Both the first solution and the second solution were added dropwise to deionized water at a precipitation temperature of 30° C. and pH controlled to 8 according to a weight ratio of cobalt:water=1:800. After addition, it was crystallized at a temperature of 60° C. for 4 hours, and centrifuged. The obtained solid product was dried at 80° C. for 10 hours, and the dried solid was calcined at 330° C. for 3 hours. The solid was reduced for 5 hours at 300° C. under a 10% $H_2$/Ar atmosphere of 7 MPa at a space velocity of 8000 $h^{-1}$, and then carbonized for 48 hours at 150° C. under a 10% CO/He atmosphere of 4 MPa at a space velocity of 2000 $h^{-1}$. Reaction was carried out with syngas of $H_2$/CO=2 as a raw gas at 230° C., under 1 MPa, and at a space velocity of 2000 $h^{-1}$. The experimental results are shown in Table 1.

Example 22

Cobalt nitrate and manganese nitrate were fully dissolved in water by stirring at a molar ratio of cobalt nitrate:manganese nitrate:water=1:0.5:25, to obtain a first solution. Sodium carbonate was fully dissolved in water by stirring at a molar ratio of sodium carbonate:water=1:25, to obtain a second solution. Both the first solution and the second solution were added dropwise to deionized water at a precipitation temperature of 30° C. and a pH controlled to 8 according to a weight ratio of cobalt:water=1:150. After addition, it was crystallized at a temperature of 60° C. for 4 hours, and centrifuged. The obtained solid product was dried at 80° C. for 10 hours, and the dried solid was calcined at 330° C. for 3 hours. The solid was reduced for 5 hours at 300° C. under a $H_2$ atmosphere of 6 MPa at a space velocity of 8000 $h^{-1}$, and then carbonized for 24 hours at 400° C. under a 10% CO/He atmosphere of 0.1 MPa at a space velocity of 20,000 $h^{-1}$. Reaction was carried out with syngas of $H_2$/CO=2 as a raw gas at 240° C., under 0.5 MPa, and at a space velocity of 4000 $h^{-1}$. The experimental results are shown in Table 1.

Example 23

Cobalt nitrate and manganese nitrate were fully dissolved in water by stirring at a molar ratio of cobalt nitrate:manganese nitrate:water=1:0.5:25, to obtain a first solution. Sodium carbonate was fully dissolved in water by stirring at a molar ratio of sodium carbonate:water=1:25, to obtain a second solution. Both the first solution and the second solution were added dropwise to deionized water at a precipitation temperature of 30° C. and pH controlled to 8 according to a weight ratio of cobalt:water=1:250. After addition, it was crystallized at a temperature of 60° C. for 4 hours, and centrifuged. The obtained solid product was dried at 80° C. for 10 hours, and the dried solid was calcined at 330° C. for 3 hours. The solid was reduced for 5 hours at 300° C. under a $H_2$ atmosphere of 0.1 MPa at a space velocity of 8000 h⁻¹, and then carbonized for 12 hours at 350° C. under a 10% CO/Ar atmosphere of 0.5 MPa at a space velocity of 8000 h⁻¹. Reaction was carried out with syngas of $H_2/CO=2$ as a raw gas at 240° C., under 0.5 MPa, and at a space velocity of 4000 h⁻¹. The experimental results are shown in Table 1.

Example 24

Cobalt nitrate and manganese nitrate were fully dissolved in water by stirring at a molar ratio of cobalt nitrate:manganese nitrate:water=1:0.5:25, to obtain a first solution. Sodium carbonate was fully dissolved in water by stirring at a molar ratio of sodium carbonate:water=1:25, to obtain a second solution. Both the first solution and the second solution were added dropwise to deionized water at a precipitation temperature of 30° C. and pH controlled to 8 according to a weight ratio of cobalt:water=1:500. After addition, it was crystallized at a temperature of 60° C. for 4 hours, and centrifuged. The obtained solid product was dried at 80° C. for 10 hours, and the dried solid was calcined at 330° C. for 3 hours. The calcined solid was subject to incipient wetness impregnation at a molar ratio of cobalt source:sodium hydroxide=1:0.001 and dried at 60° C. for 24 hours. Then, the dried solid was calcined for 3 hours at 400° C. under 0.7 MPa. The solid was reduced for 5 hours at 300° C. under a $H_2$ atmosphere of 0.2 MPa at a space velocity of 8000 h⁻¹, and then carbonized for 6 hours at 200° C. under a 10% CO/Ar atmosphere at a space velocity of 8000 h⁻¹. Reaction was carried out with syngas of $H_2/CO=2$ as a raw gas at 240° C., under 1 MPa, and at a space velocity of 4000 h⁻¹. The experimental results are shown in Table 1.

Example 25

1) Cobalt acetate and magnesium nitrate were fully dissolved in water by stirring at a molar ratio of cobalt nitrate:magnesium nitrate:water=1:1:10, to obtain a first solution. Ammonium carbonate was fully dissolved in water by stirring at a molar ratio of ammonium carbonate:water=1:200, to obtain a second solution. 2) Zirconia was stirred uniformly in water according to a weight ratio of zirconia:cobalt:water=1:0.2:10. Both the first solution and the second solution obtained in Step 1) were added dropwise to the solution obtained in Step 2) at a precipitation temperature of 90° C. and pH controlled to 9. After addition, it was crystallized at a temperature of 100° C. for 12 hours, and filtered or centrifuged. The obtained solid product was dried at 120° C. for 4 hours, and then calcined at 400° C. for 5 hours. The solid was reduced for 5 hours at 300° C. under a pure $H_2$ atmosphere of 0.1 MPa at a space velocity of 4000 h⁻¹, and then carbonized for 48 hours at 150° C. under a 10% $CO/N_2$ atmosphere of 0.9 MPa at a space velocity of 8000 h⁻¹. The carbonized solid was subjected to incipient wetness impregnation at a molar ratio of cobalt source:sodium carbonate=1:0.5, dried at 80° C. for 24 hours, and then calcined at 400° C. for 3 hours. The reaction was carried out with syngas of $H_2/CO=2$ as a raw gas at 270° C., under 0.1 MPa, and at a space velocity of 2000 h⁻¹. The experimental results are shown in Table 1.

Example 26

1) Cobalt nitrate was fully dissolved in water by stirring at a molar ratio of cobalt nitrate:water=1:60, to obtain a first solution. Potassium carbonate was fully dissolved in water by stirring at a molar ratio of potassium carbonate:water=1:100, to obtain a second solution. 2) Alumina was stirred uniformly in water according to a weight ratio of alumina:cobalt:water=1:0.4:100. Both the first solution and the second solution obtained in Step 1) were added dropwise to the solution obtained in Step 2) at a precipitation temperature of 90° C. and a pH controlled to 8. After addition, it was crystallized at a temperature of 80° C. for 72 hours, and centrifuged. The obtained solid product was dried at 80° C. for 48 hours, and the dried solid was calcined at 330° C. for 12 hours. The calcined solid was subject to incipient wetness impregnation at a molar ratio of cobalt source:lithium hydroxide=1:0.01 and dried at 100° C. for 12 hours. Then, the dried solid was calcined for 6 hours at 300° C. The solid was reduced for 8 hours at 400° C. under a 10% CO/Ar atmosphere of 0.8 MPa at a space velocity of 5000 h⁻¹ and then carbonized for 18 hours at 300° C. under a 10% CO/He atmosphere of 0.1 MPa at a space velocity of 10,000 h⁻¹. Reaction was carried out with syngas of $H_2/CO=2$ as a raw gas at 300° C., under 0.1 MPa, and at a space velocity of 2000 h⁻¹. The experimental results are shown in Table 1.

Example 27

1) Cobalt nitrate was fully dissolved in water by stirring at a molar ratio of cobalt nitrate:water=1:500, to obtain a first solution. Potassium carbonate was fully dissolved in water by stirring at a molar ratio of potassium carbonate:water=1:100, to obtain a second solution. 2) Alumina was stirred uniformly in water according to a weight ratio of alumina:cobalt:water=1:0.1:100. Both the first solution and the second solution obtained in Step 1) were added dropwise to the solution obtained in Step 2) at a precipitation temperature of 90° C. and a pH controlled to 8. After addition, it was crystallized at a temperature of 0° C. for 1 hour, and centrifuged. The obtained solid product was dried at 100° C. for 48 hours, and the dried solid was calcined at 200° C. for 24 hours. The calcined solid was subject to incipient wetness impregnation at a molar ratio of cobalt source:lithium hydroxide=1:0.1 and dried at 100° C. for 12 hours. Then, the dried solid was calcined for 6 hours at 300° C. The solid was reduced for 8 hours at 400° C. under a 10% CO/Ar atmosphere of 0.8 MPa at a space velocity of 5000 h⁻¹, and then carbonized for 18 hours at 300° C. under a 10% CO/He atmosphere of 0.1 MPa at a space velocity of 10,000 h⁻¹. Reaction was carried out with syngas of $H_2/CO=2$ as a raw gas at 300° C., under 0.1 MPa, and at a space velocity of 2000 h⁻¹. The experimental results are shown in Table 1.

Example 28

1) Cobalt nitrate was fully dissolved in water by stirring at a molar ratio of cobalt nitrate:water=1:40 AM, to obtain a first solution. Potassium carbonate was fully dissolved in water by stirring at a molar ratio of potassium carbonate:water=1:30, to obtain a second solution. 2) Alumina was stirred uniformly in water according to a weight ratio of alumina:cobalt:water=1:0.5:500. Both the first solution and the second solution obtained in Step 1) were added dropwise to the solution obtained in Step 2) at a precipitation temperature of 90° C. and pH controlled to 9. After addition, it was crystallized at a temperature of 200° C. for 48 hours, and centrifuged. The obtained solid product was dried at 80° C. for 48 hours, and the dried solid was calcined at 330° C. for 1 hour. The solid was reduced for 8 hours at 400° C. under a 10% CO/Ar atmosphere of 0.1 MPa at a space velocity of 8000 h⁻¹, and then carbonized for 24 hours at 300° C. under a 10% CO/He atmosphere of 10 MPa at a space velocity of 8000 h$^{-1}$. Reaction was carried out with syngas of H$_2$/CO=2 as a raw gas at 200° C., under 0.1 MPa, and at a space velocity of 2000 h$^{-1}$. The experimental results are shown in Table 1.

TABLE 1

Catalytic results in the presence of catalysts in the examples

| Example No | CO conversion rate (C %) | Selectivity to methane among hydrocarbons (C %) | Selectivity to olefins among hydrocarbons (C %) | Olefin product distribution (C %) | | | |
|---|---|---|---|---|---|---|---|
| | | | | C$_2$ olefin | C$_3$ olefin | C$_4$ olefin | C$_{5+}$ olefins |
| 1 | 8 | 15 | 76 | 13 | 55 | 16 | 16 |
| 2 | 58 | 6 | 81 | 28 | 22 | 23 | 27 |
| 3 | 5 | 16 | 69 | 18 | 57 | 23 | 2 |
| 4 | 10 | 18 | 74 | 16 | 38 | 24 | 22 |
| 5 | 3 | 20 | 72 | 22 | 29 | 28 | 21 |
| 6 | 7 | 18 | 68 | 18 | 35 | 25 | 22 |
| 7 | 12 | 15 | 81 | 13 | 38 | 26 | 23 |
| 8 | 20 | 10 | 67 | 18 | 36 | 26 | 20 |
| 9 | 32 | 23 | 73 | 15 | 42 | 25 | 18 |
| 10 | 28 | 21 | 78 | 19 | 35 | 25 | 21 |
| 11 | 22 | 19 | 79 | 22 | 40 | 20 | 18 |
| 12 | 35 | 30 | 80 | 31 | 32 | 21 | 16 |
| 13 | 27 | 25 | 83 | 43 | 21 | 19 | 17 |
| 14 | 45 | 19 | 72 | 28 | 43 | 18 | 11 |
| 15 | 38 | 11 | 75 | 17 | 39 | 23 | 21 |
| 16 | 32 | 12 | 81 | 21 | 36 | 23 | 20 |
| 17 | 12 | 19 | 65 | 30 | 35 | 18 | 17 |
| 18 | 29 | 20 | 82 | 30 | 41 | 16 | 13 |
| 19 | 33 | 21 | 79 | 21 | 35 | 23 | 21 |
| 20 | 18 | 19 | 59 | 16 | 35 | 28 | 21 |
| 21 | 52 | 4 | 86 | 21 | 42 | 19 | 18 |
| 22 | 45 | 8 | 79 | 15 | 37 | 24 | 24 |
| 23 | 38 | 12 | 84 | 18 | 37 | 26 | 19 |
| 24 | 42 | 16 | 76 | 23 | 41 | 26 | 10 |
| 25 | 23 | 23 | 82 | 23 | 51 | 18 | 8 |
| 26 | 61 | 43 | 32 | 50 | 31 | 11 | 8 |
| 27 | 20 | 31 | 60 | 32 | 25 | 28 | 15 |
| 28 | 30 | 15 | 80 | 22 | 35 | 24 | 19 |

As shown in Table 1, the present catalyst can be effectively used in the direct production of olefins from syngas, and has high catalytic activity, high selectivity to olefins and low selectivity to methane.

While preferred embodiments of the present invention have been described above, the present invention is not limited thereto in any way. It should be appreciated that some improvements and variations can be made by those skilled in the art without departing from the technical principles of the present invention, which are also contemplated to be within the scope of the present invention. Equivalent changes, modifications, and evolutions can be made by those skilled in the art based on the disclosure herein without departing from the spirit and scope of the present invention, which constitute equivalent embodiments of the present invention. Moreover, any equivalent changes, modifications, and evolutions made to the embodiments according to the technical essence of the present invention are still within the scope of the present invention.

What is claimed is:

1. A method of using a cobalt carbide-based catalyst for direct production of olefins from synthesis gas comprising:
   the cobalt carbide-based catalyst is made by the process comprising the following steps:
   1) mixing a cobalt source with water, or mixing a cobalt source, an electron promoter with water to obtain a first solution; and mixing a precipitant with water to obtain a second solution;
   2) adding the first solution and the second solution to water, or water and a structure promoter for precipitation, crystallizing, separating, drying and calcination; and
   3) reducing a solid obtained in Step 2) in a reducing atmosphere, and then carbonizing in a carbonizing atmosphere.
   reaction conditions comprising a reaction temperature of 150-500° C., a reaction pressure of 0.1-10 MPa, a gas hourly space velocity of 40,000-100,000 h$^{-1}$, and a molar ratio of H$_2$ to CO is (1:10)-(10:1).

2. The method of using a cobalt carbide-based catalyst for direct production of olefins from synthesis gas according to claim 1, wherein the reaction is carried out in a fixed bed, a slurry bed or a fluidized bed.

* * * * *